(12) United States Patent
Valjakka et al.

(10) Patent No.: US 7,549,749 B2
(45) Date of Patent: Jun. 23, 2009

(54) VISUAL STIMULATOR

(75) Inventors: Antti Valjakka, Saunarannantie 27, FIN-71570 Syvänniemi (FI); Arto Urtti, Kuopio (FI); Janne Ahonen, Kuopio (FI)

(73) Assignee: Antti Valjakka, Syvanniemi (FI)

( * ) Notice: Subject to any disclaimer, the term of this patent is extended or adjusted under 35 U.S.C. 154(b) by 778 days.

(21) Appl. No.: 10/974,866

(22) Filed: Oct. 26, 2004

(65) Prior Publication Data

US 2005/0131498 A1 Jun. 16, 2005

Related U.S. Application Data

(63) Continuation of application No. PCT/FI03/00351, filed on May 5, 2003.

(30) Foreign Application Priority Data

May 6, 2002 (FI) .................................. 20020851

(51) Int. Cl.
*A61B 3/10* (2006.01)
*A61B 3/02* (2006.01)

(52) U.S. Cl. .................. 351/221; 351/205; 351/222; 351/243

(58) Field of Classification Search ........... 351/221, 351/205, 210, 216, 222, 233, 243
See application file for complete search history.

(56) References Cited

U.S. PATENT DOCUMENTS

| 4,255,023 A | 3/1981 | House | 351/226 |
| 4,618,230 A | 10/1986 | Ens et al. | 351/221 |
| 5,416,336 A * | 5/1995 | Koivulehto | 250/584 |
| 5,506,633 A | 4/1996 | Sperling | 351/206 |

FOREIGN PATENT DOCUMENTS

| DE | 43 01 483 A1 | 8/1994 |
| SU | 1648336 A1 | 5/1991 |
| WO | WO-01/78586 A1 | 10/2001 |
| WO | WO-02/41768 A1 | 5/2002 |

OTHER PUBLICATIONS

Hawlina, M. et al., "HK-Loop Ag Fibre Electrode for Clinical Eletroretinography", 1992, Documenta Ophthalmalogica 81, pp. 252-259.
Bayer, A. et al., "Comparisons of the Amplitude Size and the Reproducibility of Three Different Electrodes to Record the Corneal Flash Electroretinogram in Rodents", 2000, Documenta Ophthalmalogica 98, pp. 233-246.

\* cited by examiner

*Primary Examiner*—Ricky L Mack
*Assistant Examiner*—Brandi N Thomas
(74) *Attorney, Agent, or Firm*—Harrington & Smith, PC

(57) ABSTRACT

The present invention relates to a visual stimulator, which comprises a light stimulation source, a regulable attenuator of light, mirrors for reflecting light and light detectors. The visual stimulator in accordance with the invention comprises a mirror chamber and a mirror tube constructed of mirrors in which the reflecting points of the mirrors form various angles with respect to each other, and which have been connected to each other such that light beams disperse from the mirror tube to the mirror chamber without hindrance regardless of the location of the object to be examined or a part of it in the mirror chamber and though the location of the object or a part of it would vary in certain limits in the mirror chamber, and that to one end of the mirror tube, viewed away from the mirror chamber a light stimulation source has been directed.

22 Claims, 2 Drawing Sheets

VISUAL STIMULATOR

CROSS REFERENCE TO RELATED APPLICATION

This application is a continuation of International Patent Application No. PCT/FI03/00351 filed May 5, 2003.

The present invention relates to a visual stimulator, which comprises a light stimulation source, a regulable attenuator of light, mirrors for reflecting light and light detectors.

BACKGROUND OF THE INVENTION

There are two technical requirements in stimulating techniques applied in visual measurement methods for creating a visual response: the way the visual stimulus has been pointed to the eye and the way other factors of the stimulus source than factors of light effect have been eliminated from the object for measurement. In visual measurement methods based on recognized techniques which have been designed for measuring the physiological potential change of retina of the eye (electroretinogram, ERG) for a visual stimulus carried out on test animals has been represented that by applying mirrors, lenses or a LED-light source or a flashlight aligned to the eye the beams of the light may be pointed to the retina and to various parts of it while the subject to be examined stays on place or has by some means made immovable. (Documenta Ophthalmologica 98, 2000, Bayer A. U., Mittag T., Cook P., Brodie S. E., Podos S. M. and Maag K-P. "Comparisons of the amplitude size and the reproducibility of three different electrodes to recorded the corneal flash electroretinogram in rodents", p. 233-246; Documenta Ophthalmalogica 81, 1992, Hawlina M. and Konec B., "New noncorneal HK-loop electrode for clinical electroretinography", p. 253-259; U.S. Pat. No. 4,255,023; U.S. Pat. No. 5,506,633; SU-patent publication 1 648 336).

The measuring of ERG-potentials corresponding with the magnitude of visual stimulus from a laboratory animal or a human moving freely creates a technical problem because in free motion the direction of gaze in 3-dimensional space as well as the place of the body or a part of it such as the head continuously changes between different measurements. Another common technical problem while applying some visual stimulus sources, such as a flashlight, are other physical effects created by them than the changes in light intensity, which other physical effects may be the change in magnetic field and sound, among other things. The solving of the problem should effect such that the magnitude of the visual sense is independent of the direction of the gaze of the subject, the body or a part of it may not hinder the transmitting of the visual stimulus and other than light effects of the light stimulus source are excluded in the object for measuring.

The object of the invention is to eliminate these disadvantages and to provide a visual stimulator, which enables the registration of an ERG-response created by a visual stimulus as well as registration of other biopotential responses connected with other visual processes from a laboratory animal or a human moving freely and being conscious such that the direction of the gaze or the place of the body or a part of the body, such as the head, must not be constant between different measuring situations. In addition, the object of the invention is to provide a device which excludes other than light stimulating factors, which other factors might arise from the applying of the light stimulating source.

DESCRIPTION OF THE INVENTION

The visual stimulator in accordance with the invention comprises a mirror chamber and a mirror tube constructed of mirrors, in which chamber and tube the reflecting sites of the mirrors form various angles with respect to each other, and which sites have been connected to each other such that light beams are dispersed from the mirror tube to the mirror chamber without hindrance regardless of the location of the object or a part of an object to be examined in the mirror chamber, and to the other end of the mirror tube, as seen away from the mirror chamber, a light stimulating source has been aligned.

The above mentioned purposes are achieved by applying a visual stimulator in accordance with the invention, which stimulator comprises a mirror chamber and a mirror tube, which have been connected to each other such that while a laboratory animal to be examined, or some other biological object such as the head of a human has been placed in the mirror chamber light beams are dispersed from the mirror tube to the mirror chamber without hindrance regardless of the location of the object or a part of an object to be examined in the mirror chamber. An even dispersion of light beams in the mirror chamber is created by parts of the mirror surfaces of the mirror chamber and mirror tube located in various angles with respect to each other, while the magnitude of the exposition of the object for a visual stimulus is independent of the change of the direction of the gaze, which may be caused by eye movements or the change in place of the body. Light is reflected from a light stimulus source, such as a flashlight, to disperse to a closed mirror tube the inner surfaces of which are reflecting and through it such that the distance that the mirror tube forms from light stimulus source to the mirror chamber, in its part, excludes other factors than the desired change in light intensity in the mirror chamber. A change in magnetic field and sound while applying a flashlight may be, for example, these kind of non-light effecting factors caused by light stimulus source.

While more than one light stimulating source are applied in the solution in accordance with the invention presented above the dynamic function of visual sense may be measured for visual stimuli presented in variable time sequences, which visual stimuli may be discrete or in various ways cumulatively overlapping with respect to time and intensity.

In addition, while the photon flow of each visual stimulus, which may be a light flash of short duration, is selectable regulable according to its wave length it is possible to modulate the spectrum of factors having influence on the visual stimulation as desired: the sequence or state of cumulation in time of the stimulation, the chromatic characteristics of the stimulation and the intensity of the stimulation and such measure the general dynamics of sight.

DESCRIPTION OF THE DRAWINGS

Next, the invention will be explained in more detail with reference to the accompanying drawings, in which.

Figure 1:
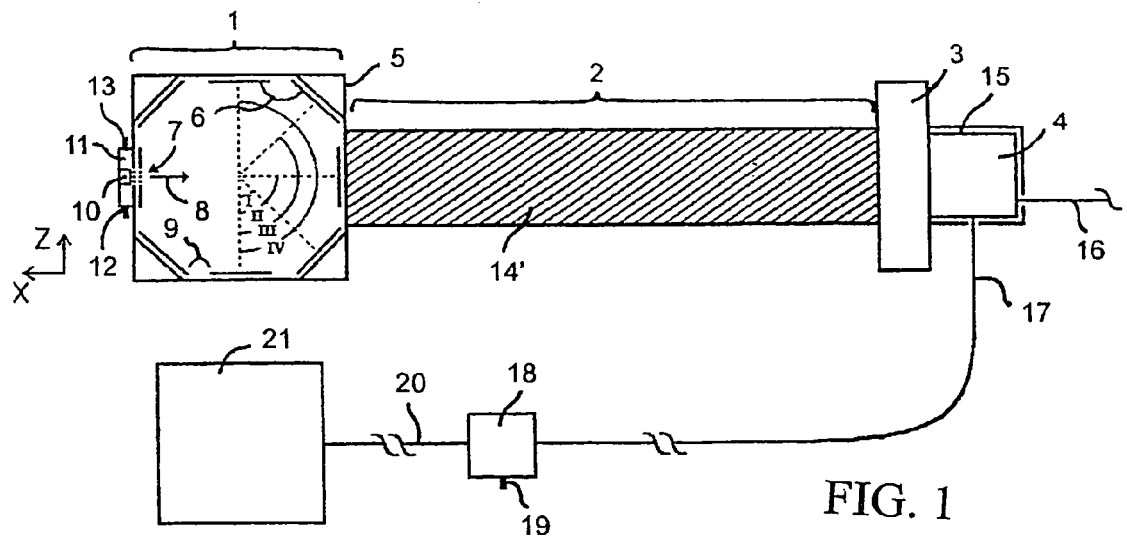
FIG. 1 illustrates a visual stimulator in accordance with the invention viewed from above.

The visual stimulator in accordance with the figures comprises a mirror chamber 1 constructed of one or several mirrors 6 and a mirror tube 2 constructed of one or several mirrors 14 and which tube is connected to the chamber. In addition, the visual stimulator comprises a light stimulation source 4 placed in the other end of the mirror tube, an attenuator device 3 as well as photodetectors 11 and 18.

Figure 4:
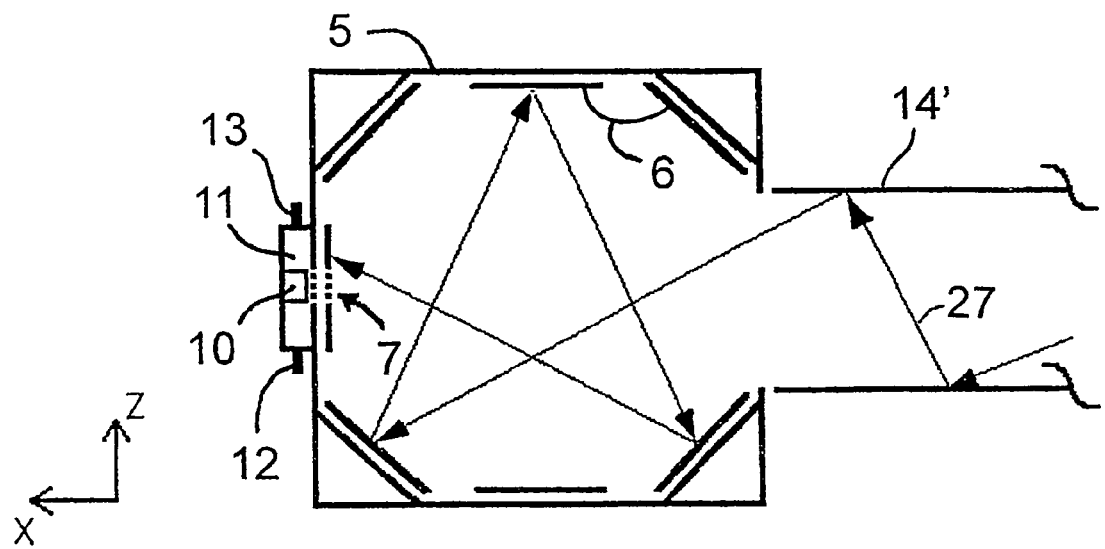
FIG. 4 illustrates the path of a light beam in a visual stimulator in accordance with FIG. 1.
Figure 5:
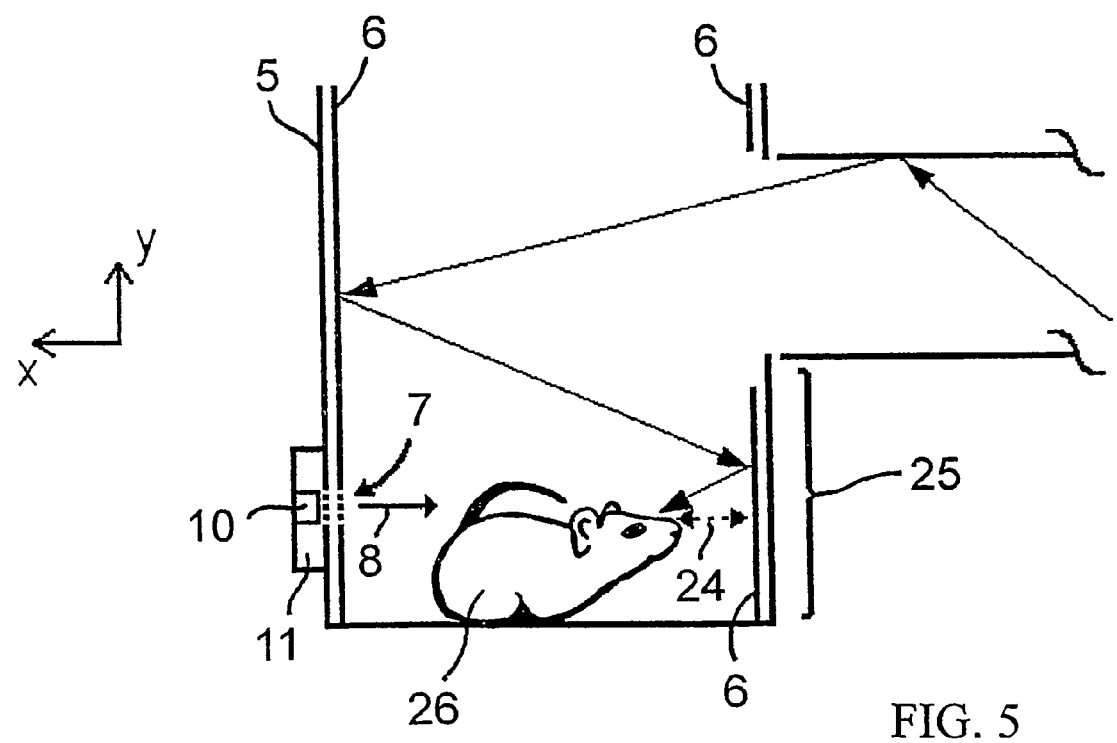
FIG. 5 illustrates the path of a light beam in a visual stimulator in accordance with FIG. 2.

The mirror chamber 1 comprises an outer wall 5, which has been made of transparent material in this application, such as Lexan-plastic, advantageously, or corresponding or glass, and it gives limits to a square bottom area forming a tetrahedron left open in one end. The bottom of the tetrahedron may be constructed removable for cleaning possibility. On the inner surface of the chamber 1, in symmetric order viewed from above, mirrors 6 have been adjusted such that there are gaps 9, illustrated in FIG. 1, left between the mirrors for observing the space for a laboratory animal 26 in accordance with FIGS. 4 and 5. The reflecting surface 6 of the mirrors is facing inside the chamber 1. The mirrors 6 in the mirror chamber 1 form various angles with respect to each other (angles I, II, III, IV in FIG. 1 for example). In this application the mirrors 6 are planelike and placed such that the angle I equals 45°, the angle II 90°, the angle III 135° and the angle IV 180°. In the other application mirrors may be unlimited curved. The silver surface 6' of all mirrors has been earthened to the same 0-potential of the system.

Figure 3:
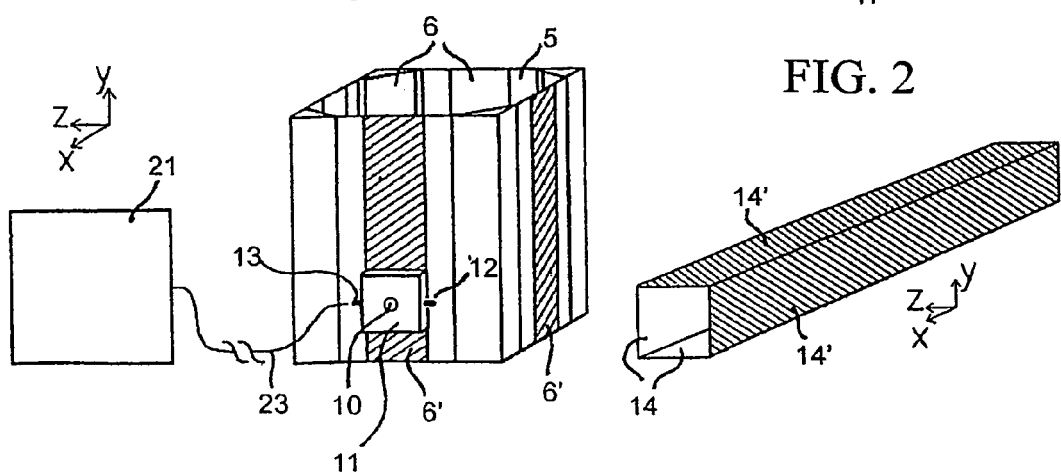
FIG. 3 illustrates parts of a visual stimulator in accordance with FIG. 1 viewed separately inclined from side.

Against one outer wall, viewed from outside, of the mirror chamber 1 a photodetector 11 has been adjusted such that the observing line 8 of the sensor 10 in it is directed through an opening 7 placed on the outer wall 5 and in the mirror 6 to the mirror chamber 1 such that the photodetector 11 observes the light intensity in the mirror chamber 1. The sensor 10 of the photodetector 11 has been placed in vertical direction to correspond with the horizontal level 24 of the visual field of the laboratory animal 26. The voltage pulse describing the intensity of light measured by the photodetector 11 is transmitted from the outlet connector 13 with a conductor 23 to the automatic data processing device 21 illustrated in FIGS. 1 and 3 for registration and storing, where the intensity of light as a function in time may be determined. The photodetector 11 may employ external voltage as its power source, which voltage is transmitted to the connector 12. There may be more than one photodetector in the mirror chamber.

Figure 2:
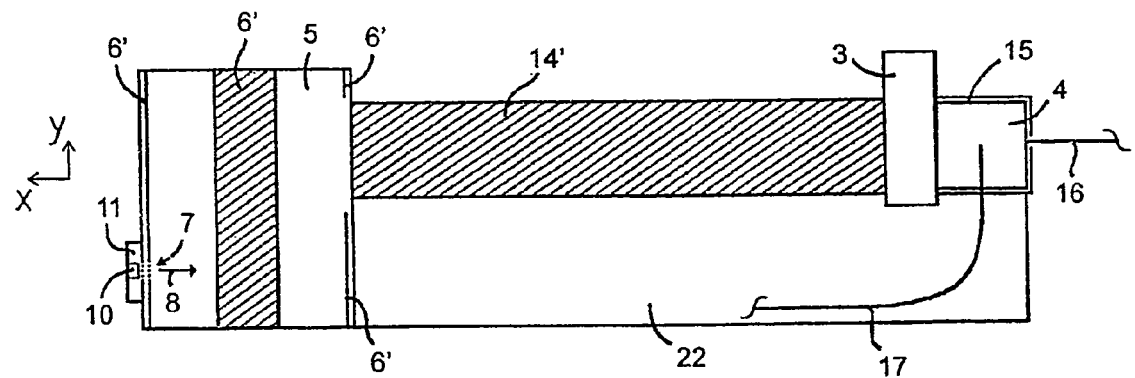
FIG. 2 illustrates a visual stimulator in accordance with FIG. 1 viewed from side.

The mirror tube 2 open in the ends and square by cross-section has been directed against one outer wall of the mirror chamber 1 viewed from outside. The reflecting surfaces 14 of the mirrors of the mirror tube form the inner wall of the tube 2. In the connection point of the mirror tube 2 and the mirror chamber 1 on the wall of the mirror chamber 1 there is an opening corresponding with the cross-sectional area of the mirror tube 2 or optionally at this point on the inner surface of the outer wall 5 of the mirror chamber 1 there are no mirrors. The mirror tube 2 has been supported on a stand 22 in accordance with FIG. 2 on the height 25 where the body or a part of the body of a laboratory animal 26 may not hinder the dispersion of light beams from the mirror tube 2 to the mirror chamber 1. The silver surface 14' of all mirrors of the mirror tube has been earthened to the same 0-potential of the system. The mirrors 14 in this application are planelike mirrors. In the other application the mirrors may be unlimited curved.

In the end of the mirror tube, viewed away from the mirror chamber, there is the light stimulation source 4, the light reflecting surface of which has been directed to the mirror tube 2. The light stimulation source 4 has been covered with metal protection cover 15, excluding the surface reflecting light, which cover has been earthened to the 0-potential of the system. The metal protection cover has been manufactured, advantageously, of a metal plate of sufficient thickness (about 2 mm for example), in order, for its part, to eliminate the influence of the magnetic field and sound created by the light stimulation source 4 on the measuring system and the subject 26 to be examined in the mirror chamber 1. The light stimulation source 4 may be activated either with a switch on it, electronically with a conductor 16 or wirelessly with a remote control, the field pulse of which is such that it has no influence on other parts of the device than on the light stimulation source 4 to be controlled. Light beams 27 reflect from the light stimulation source 4 through a regulated attenuator 3 placed between the light stimulation source 4 and the mirror tube 2 to the mirror tube 2, where they are dispersed and from where they continue further to the mirror chamber 1.

The attenuator 3 has been organized to attenuate various wavelengths of light with optional efficiencies. In the other application the attenuator of the light intensity has been placed between the mirror tube and the mirror chamber.

There is a fibre optics cable 17 connected to the light stimulation source 4, which fibre optics cable conducts light created by the light stimulus source 4 to the photodetector 18, where from the information about the intensity of light is transmitted through an electronic conductor 21 to be registered and stored. The optic isolation technique described enables comparing of light intensity of the light stimulation source 4 with the induced ERG-response as a function of time as well as the fact that the biopotential signal is free of disturbance, which could be transmitted from conductors in case they were connected to the light stimulation source 4 or near to it.

Photodetectors 11 and 18 comprise a phototransistor and/or a photodiode as well as an operation amplifier amplifying the light signal. Silver surfaces 6' and 14' of all mirrors 6 and 14 of the device as well as the metal protection cover 15 have been galvanically connected to each other.

In accordance with what above has been presented the biological object placed in the mirror chamber may be only a head of a subject, of a human, for example. The chamber may be lowered down by means of supporting rods round the sitting test subject's head. In this case it is practical that the mirror tubes overlap mutually into spiral curves (see claims).

In accordance with the idea of the invention the mirror tube 2 is employed as focusing device of light beams from the light stimulation source 4 to that point of the mirror chamber 1 where the subject 26 may not form a hindrance for light dispersion from the mirror tube 2 to the mirror chamber 1. The mirror tube 2 enables the light reflection to the mirror chamber 1 from such a distance that it, for its part, eliminates other effects (change in magnetic field, sound stimulus) of the light stimulation source 4 than changes of the light intensity in the mirror chamber 1. The mirror chamber 1 functions as a space where a laboratory animal 26 may freely move around in a limited area and where light beams disperse evenly in 3-dimensional space when the mirror chamber 1 as well as the mirror tube 2 connected to it have been made of mirrors 6 and 14, which mirrors or their reflecting parts form various angles with respect to each other.

Within the limits of the invention also other than above described solution may be considered. Such, the mirror tube may be of any shape and of any size, it may be made of one or several mirrors and it or those may be directed to the mirror chamber from different directions such, however, that the principle stays as presented. For example, a conical mirror tube may be directed vertically to the upper part of the mirror chamber. The number of mirror tubes or light stimulation sources is not limited. In the same way the mirror chamber in accordance with the presented principle may be of any shape and size and it may be made of one or several mirrors. As a light stimulation source a glow bulb or some other recognized source of light instead of a flashlight may be applied.

The invention is not limited to the presented advantageous application but it can vary within the frames of the idea of the invention formed in the claims.

What is claimed is:

1. A visual stimulator, which includes
a light stimulation source, a regulable attenuator of light, mirrors for reflecting light and light detectors,
a mirror chamber and a mirror tube constructed of mirrors in which the reflecting points of the mirrors form various angles with respect to each other,
said mirror chamber and said mirror tube have been connected to each other such that light beams disperse from the mirror tube to the mirror chamber without hindrance regardless of the location of the object to be examined or a part of it in the mirror chamber and though the location of the object or apart of it would vary in certain limits in the mirror chamber,
and that to one end of the mirror tube viewed away from the mirror chamber an equipped light stimulation source has been directed.

2. A visual stimulator according to claim 1, in which there is one or several mirrors in the mirror chamber.

3. A visual stimulator according to claim 1, in which the mirror of the mirror chamber is planelike.

4. A visual stimulator according to claim 1, in which the mirror of the mirror chamber is unlimited curved.

5. A visual stimulator according to claim 1, in which there is one or several mirrors in the mirror tube.

6. A visual stimulator according to claim 5, in which the mirror of the mirror tube is planelike.

7. A visual stimulator according to claim 1, in which the mirror of the mirror tube is unlimited curved.

8. A visual stimulator according to claim 1, in which unlimited number of mirror tubes have been directed to the mirror chamber.

9. A visual stimulator according to claim 1, in which an outer wall of the mirror chamber has been made of transparent material.

10. A visual stimulator according to claim 9, in which the outer wall of the mirror chamber has been made of plastic or glass.

11. A visual stimulator according to claim 1, in which that there are openings between the mirrors of the mirror chamber.

12. A visual stimulator according to claim 1, in which a regulable attenuator of light has been placed between the light stimulation source and the mirror tube.

13. A visual stimulator according to claim 1, in which a regulable attenuator of light has been placed between the mirror tube and the mirror chamber.

14. A visual stimulator according to claim 1, which includes unlimited number of light stimulation sources.

15. A visual stimulator according to claim 1, in which more than one light stimulation source has been directed to the mirror tube.

16. A visual stimulator according to claim 1, in which the light stimulation source (4) is a flashlight.

17. A visual stimulator according to claim 1, in which the light stimulation source has been covered with metal protection cover excluding its light-reflecting surface.

18. A visual stimulator according to claim 1, in which a fibre optics cable has been connected to the light stimulation source, which cable has been connected to the light detector from where the information about light intensity is to be conveyed to the data processing device.

19. A visual stimulator according to claim 1, in which in the mirror chamber there is one or several light detectors, from which the information about light intensity is to be conveyed to the data processing device.

20. A visual stimulator according to claim 1, in which the light detectors comprise a phototransistor and/or a photodiode as well as an operation amplifier amplifying the light signal.

21. A visual stimulator according to claim 1, in which silver surfaces of all mirrors of the device as well as a metal protection cover of the light stimulation source have been galvanically connected to each other.

22. A visual stimulator according to claim 1, in which a regulable attenuator of light has been organized to attenuate various wavelengths of light on selectable efficiency.

* * * * *